United States Patent [19]
Cook et al.

[11] Patent Number: 5,319,084
[45] Date of Patent: Jun. 7, 1994

[54] HEXAHYDROINDENOPYRIDINE COMPOUNDS HAVING ANTISPERMATOGENIC ACTIVITY

[75] Inventors: C. Edgar Cook, Staunton, Va.; Yue-Wei Lee, Chapel Hill, N.C.; Mansukh C. Wani, Durham, N.C.; Patricia A. Fail, Rtp, N.C.; Joseph M. Jump, Efland, N.C.

[73] Assignee: Research Triangle Institute, Research Triangle Park, N.C.

[21] Appl. No.: 106,655

[22] Filed: Aug. 16, 1993

[51] Int. Cl.$^5$ .................. C07D 221/16; A01N 43/42; A61K 31/44
[52] U.S. Cl. ........................................ 546/111; 546/79
[58] Field of Search .................. 546/111, 79; 514/290

[56] References Cited

U.S. PATENT DOCUMENTS

| | | | |
|---|---|---|---|
| 2,470,108 | 5/1949 | Plati et al. | 546/111 |
| 2,470,109 | 5/1949 | Plati et al. | 546/111 |
| 2,546,652 | 3/1951 | Plati et al. | 546/111 |
| 3,408,353 | 10/1968 | Jucker et al. | 546/111 |
| 3,462,443 | 8/1969 | Paragamian | 546/111 |
| 3,497,517 | 2/1970 | Jucker et al. | 546/111 |
| 3,574,686 | 4/1971 | Jucker et al. | 546/111 |
| 3,627,773 | 12/1971 | Ebnother et al. | 546/111 |
| 3,678,057 | 7/1972 | Ebnother et al. | 546/111 |
| 3,678,058 | 7/1972 | Ebnother et al. | 546/111 |
| 3,991,066 | 11/1976 | Bastian et al. | 546/111 |
| 4,103,014 | 7/1978 | Hodel | 424/267 |

OTHER PUBLICATIONS

Burger, *Medicinal Chemistry*, 3rd edition, p. 52, 1970.
Mutation Research, (1979), vol. 66, pp. 113-127, "Actions of an Antispermatogenic, but Non-Mutagenic, Indenopyridine Derivative in Mice and Salmonella Typhimurium", Matter et al.
Arch. Toxicol. (1984), Suppl. 7, pp. 171-173, "Effects of an Indenopyridine Derivative, Compound 20-438, on Spermatogonial Stem Cells of the Rat", Suter.
Arch. Toxicol., (1978), Suppl 1, pp. 323-326, "Reversible Inhibition of Spermatogenesis with an Indenopyridine (20-438)", Hodel et al.

*Primary Examiner*—C. Warren Ivy
*Assistant Examiner*—D. Margaret M. Mach
*Attorney, Agent, or Firm*—Oblon, Spivak, McClelland, Maier & Neustadt

[57] ABSTRACT

Hexahydroindenopyridine compounds having the following formula and relative stereochemistry

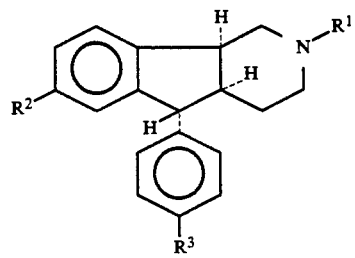

where $R^1$ is $C_{1-6}$ alkyl, $R^2$ is hydrogen or $C_{1-6}$ alkyl and $R^3$ is carboxyl or a group which is metabolized to a carboxyl group under mammalian physiological conditions exhibit potent antispermatogenic activity and are useful in a method of inhibiting spermatogenesis in mammals.

31 Claims, 3 Drawing Sheets

| COMPOUND# | R¹ | R² | R³ | R⁴ |
|---|---|---|---|---|
| A-2 | Et | Me | Me | H |
| A-2l [(−)-ENANTIOMER] | Et | Me | Me | H |
| A-2d [(+)-ENANTIOMER] | Et | Me | Me | H |
| A-10 | H | Me | Me | H |
| A-11 | Me | Me | Me | H |
| A-24 | Et | Me | H | o-Me |
| A-26 | Et | Me | H | m-Me |
| A-28 | Et | Me | F | H |
| A-29 | Et | Me | OMe | H |
| A-30 | Et | Me | CHO | H |
| A-37 | Et | H | H | H |
| A-38 | Et | Me | H | H |
| A-40 (4a,5-DOUBLE BOND) | Et | Me | Me | H |
| A-41 | Et | H | Me | H |
| A-42 | Et | Me | Me | Me |
| A-45 | n-Pr | Me | Me | H |
| A-46 | i-Pr | Me | Me | H |
| A-54 | Et | Me | COOH | H |
| A-55 | Et | Me | CH$_2$OH | H |
| A-56 | Et | Me | COOMe | H |
| A-57 | Et | Me | CONH$_2$ | H |
| A-58 | Et | Me | CONMe$_2$ | H |
| A-59 | Et | Me | CH$_2$OC(O)NHMe | H |
| A-60 | Et | Me | CN | H |
| A-61 | Et | Et | Me | H |
| A-62 | Et | Me | COO-n-Pr | H |
| A-63 | Et | Me | CH=NH-NHCONH$_2$ | H |
| A-64 | Et | Et | COOMe | H |

FIG. 3

HEXAHYDROINDENOPYRIDINE COMPOUNDS HAVING ANTISPERMATOGENIC ACTIVITY

BACKGROUND OF THE INVENTION

1. Field of the Invention

The present invention is directed to hexahydroindenopyridine compounds which interrupt spermatogenesis and cause infertility. These compounds are useful as contraceptive agents in human males and for control of the fertility of domestic, wild and feral animals.

2. Discussion of the Background

Safe and effective orally active male contraceptive drugs have been sought for many years. However, the development of a drug which can safely interrupt spermatogenesis without affecting libido and thereby function as a male contraceptive agent has proven to be a difficult task.

An ideal contraceptive for the male would be one that effectively arrests the production of spermatozoa or blocks their fertilizing capacity without affecting libido or accessory sex organs and their functions. In addition, it should have a wide separation of effective and toxic doses, and the method should be reversible. Such an ideal male contraceptive agent is currently unavailable.

Some general cellular toxicants such as anticancer agents and alkylating agents affect spermatogenesis, but are obviously not acceptable as contraceptives. Compounds which interfere with cellular energy processes, such as thiosugars also interfere with spermatogenesis, but are not sufficiently selective. Androgens such as testosterone and its analogs, when given in sufficiently high doses, interfere with spermatogenesis, probably through a mechanism involving the hypothalamic-pituitary axis. These steroid compounds have been used successfully in clinical studies. However, the anabolic properties of these steroids may give rise to undesirable side effects.

Gonadotrophin releasing hormone (GNRH) analogs have been actively investigated as compounds which effectively block spermatogenesis. However, GNRH analogs interfere with endogenous testosterone production and thus decrease libido unless supplementary androgens are administered.

One approach to male contraceptives is based on identification and exploitation of the biochemistry of the male reproductive process. The testis consists of three functional compartments. The first, responsible for the production of sperm, consists of seminiferous tubules which contain developing germ cells. The second is the Sertoli cell, also located inside the seminiferous tubule, which contributes to the organizational and functional coordination of the spermatogenic process and probably has paracrine and autocrine roles. Due to the complex organizational relationship between the Sertoli cell and the developing germ cells, and the presence of tight junctions between neighboring Sertoli cells, a blood testis barrier is formed, dividing the seminiferous tubule into areas that are isolated from the direct access by blood-borne chemicals or nutrients. Surrounding the tubules, in the interstitial tissue, are Leydig cells that have several endocrine and paracrine functions, the production of testosterone being the best described.

The germinal cells divide and differentiate progressively, moving as they mature from the basement membrane to the tubule lumen. Spermatogonia lie in the basal compartment, and selectively recruited spermatogonia divide mitotically to become either cells that persist as spermatogonia or differentiate into primary spermatocytes. The primary spermatocytes migrate through the junctions between the Sertoli cells and divide meiotically to form secondary spermatocytes. Secondary spermatocytes divide to form spermatids. The spermatids then differentiate into mature spermatozoa. Differentiation of the spermatids is termed spermatogenesis.

A summary of Sertoli cell functions is as follows: (a) support and nutrition to the seminiferous epithelium, (b) release of late spermatids into the tubule lumen, (c) formation of a morphological and physiologic blood testes barrier, (d) phagocytosis of degenerating germ cells, and (e regulation of the cycle of seminiferous epithelium.

The Leydig cell also supports spermatogenesis. Luteinizing hormone (LH) from the pituitary stimulates testosterone production by the Leydig cell. Testosterone and its metabolite, dihydrotestosterone, are necessary to support normal spermatogenesis. Testosterone receptors are present on various germ cell types. Testosterone is delivered through the blood testis barrier, likely through transport into the Sertoli cell, where it is metabolized into estradiol, dihydrotestosterone, or remains unaltered.

Some, if not all of the germ cell types, interact with the Leydig and/or Sertoli cell. These interactions are in the form of chemical messengers that are produced by Sertoli, Leydig, and germ cell(s). For example, the pachytene spermatocyte modulates the secretion of a Sertoli cell proteinaceous factor that in turn stimulates steroidogenesis by the Leydig cell. The binding of spermatids occurs only to Sertoli cells which are rendered competent or functional by exposure to FSH. The Sertoli cell of rats secretes several proteins in a cyclic fashion, with maximal production occurring at a specific stage of the seminiferous epithelium; that is, when it is in association with a specific group of germ cells. Clusterin is produced maximally by Sertoli cells when the seminiferous epithelium is in a Stage VII or VIII configuration that is independent of FSH stimulation, suggesting a local regulation of Sertoli secretory function by germ cells.

Hexahydroindenopyridine compound no. 20,438 developed by Sandoz, Ltd. (referred to below as A-2) has been shown to provide reversible inhibition of spermatogenesis on oral administration to animals. See *Arch. Toxicol. Suppl.*, 1984, 7:171-173; *Arch. Toxicol. Suppl.*, 1978, 1:323-326; and *Mutation Research*, 1979, 66:113-127.

The synthesis of a variety of indenopyridine compounds as racemic mixtures is known and described, for example, in U.S. Pat. Nos. 2,470,108; 2,470,109; 2,546,652; 3,627,773; 3,678,057; 3,462,443; 3,408,353; 3,497,517; 3,574,686; 3,678,058 and 3,991,066. These indenopyridine compounds have a variety of uses including use as serotonin antagonists exhibiting antiphlogistic and analgesic properties, hematoblast aggregation inhibitors, sedatives, and neuroleptic compounds as well as ulcer-protective, hypotensive and anorexigenic compounds.

Despite extensive research in this field, a need continues to exist for orally active reversible male antifertility drugs which have limited side-effects.

SUMMARY OF THE INVENTION

Accordingly, one object of the present invention is to provide an orally active male contraceptive drug which does not affect libido and has minimal side effects or toxicity.

A further object of the present invention is to provide an orally active male contraceptive drug which reversibly inhibits spermatogenesis and a method of inhibiting spermatogenesis using this drug.

These and other of the objects of the present invention have been achieved by the discovery of the hexahydroindenopyridine compounds of the present invention and the discovery that these compounds interrupt spermatogenesis in contrast to similar compounds which are inactive.

DETAILED DESCRIPTION OF THE PREFERRED EMBODIMENTS

It has now been discovered that hexahydroindenopyridine compounds having the structure (I) shown below wherein the hydrogen atoms at positions 4a, 5 and 9b have the relative stereochemistry shown (hydrogens at positions 4a and 5 are trans, hydrogens at 4a and 9b are cis to one another) and where $R^1$ is straight-chain or branched $C_{1-6}$ alkyl, preferably $C_{1-3}$ alkyl, $R^2$ is hydrogen, straight-chain or branched $C_{1-6}$ alkyl, preferably $C_{1-3}$ alkyl, and $R^3$ is carboxyl (COOH) or a group which can be converted under mammalian physiological conditions to a carboxyl group are antispermatogenic.

The compounds of the present invention have the relative stereochemistry shown in structure (I). This invention includes both individual enantiomeric forms (essentially optically pure) as well as any mixtures of these forms, for example, a racemic mixture.

Pharmaceutically acceptable salts of the compounds having structure (I) shown above are also included within this invention. Pharmaceutically acceptable salts include, but are not limited to salts with inorganic acids such as hydrochloride, sulphate, phosphate, diphosphate, hydrobromide and nitrate or salts with an organic acid such as acetate, malate, maleate, fumarate, tartrate, succinate, citrate, lactate, methanesulfonate, p-toluenesulfonate, palmoate, salicylate and stearate.

Substituent $R^1$ is preferably a straight-chain alkyl (n-alkyl) or iso-alkyl group, such as methyl, ethyl, n-propyl, iso-propyl, n-butyl, iso-butyl, n-pentyl, iso-pentyl, n-hexyl and iso-hexyl. Most preferably, $R^1$ is ethyl. Substituent $R^2$ is also preferably a straight-chain or iso-alkyl group as was $R^1$ described above. Substituent $R^3$ is preferably hydroxymethyl ($CH_2OH$), formyl (CHO), carboxyl (COOH), carboxylic acid ester (COOR where R is $C_{1-10}$ alkyl, $C_{6-10}$ aryl, $C_{7-10}$ aralkyl), and hydroxymethyl esters ($CH_2OC(O)$—R where R is as defined above). The potent activity of these compounds is surprising.

Compound A-2 (Sandoz, Ltd.) is a racemic mixture of the compound shown below.

Hexahydroindenopyridines such as A-2 and the compounds of the present invention have three asymmetric centers which can be defined using known nomenclature. Alternatively the relative stereochemistry can be defined by the cis-trans relationships of the hydrogen atoms bonded to the carbon system at positions 4a, 5 and 9b of the tricyclic ring system, leading to the stereochemical assignments in FIG. 1. Following this nomenclature, the stereochemistry of compound A-2 was found to be (4aRS,5SR,9bRS)-2-ethyl-2,3,4,4a,5,9b-hexahydro-7-methyl-5-(4-methylphenyl)-1H-indeno[1,2-c]pyridine.

Compound A-2 has a hydrophobic methyl substituent on the 5-phenyl group corresponding to substituent $R^3$ in structure (I) shown above. It has now been discovered that the antispermatogenic activity of A-2 resides exclusively in the (+) isomer, which is an effective antispermatogenic drug in mice. It has also been discovered that replacing the $R^3$ methyl group of A-2 with a slightly less hydrophobic hydrogen atom or with a more polar methoxy group abolishes activity.

The very polar carboxyl group or groups which can be metabolized under mammalian physiological conditions to a carboxyl group may be present at the para-position of the 5-phenyl ring with retention of antispermatogenic activity. For example, compounds in which the para-position is substituted with hydroxymethyl ($CH_2OH$), formyl (CHO), carboxyl (COOH) and methoxycarbonyl ($C(O)OCH_3$) groups retain potent antispermatogenic activity. These compounds exhibit oral antispermatogenic activity despite the presence of a polar substituent in the para-position of the 5-phenyl ring.

By "metabolized under mammalian pysiological conditions" is meant a functional group $R^3$ which is converted to a carboxyl group when a compound having structure (I) is administered to a living mammal for which antispermatogenic treatment is desired. Administration may be oral, intraperitoneal or intravenous. The conversion of the group $R^3$ to a carboxyl group is determined by monitoring metabolites of the compound having structure (I) in the blood or in the urine. The metabolites may be monitored using conventional analysis methods such as mass spectrometry (MS), gas chromatography (GC), etc.

The antispermatogenic activity of compound A-2 is observed after a single oral dose of 30 mg/kg to rats, drastically reducing the weights of the testes within 24 h. Degenerative changes in the seminiferous tubules are observed. Spermatids became pycnotic, occasionally forming multinucleated associations. Sertoli cells appear to be cytologically normal. It appears that compound A-2 targets spermatids or the Sertoli cell associated with these spermatids because histologic changes are observed in these spermatids first.

Compound A-2 causes some lethargy and sedation in mice at an oral dose of 30 mg/kg and extreme lethargy at the same dose given subcutaneously. Lethargy and sedation are obviously undesirable side effects in contraceptive agents. In contrast to the lethargy and sedation observed with A-2, the compounds of the present invention produce minimal lethargy.

The compounds of the present invention allow one to separate the antifertility activity from the sedative activity observed with compound A-2. The compounds of the invention are, therefore, effective antifertility drugs in which the undesired side-effects of sedation and lethargy are markedly diminished.

Compounds were screened for antispermatogenic activity by dosing male mice on day 1 with a gavage dose of control vehicle, positive control (A-2) or compound of the invention. At 72 h after dosing, animals were killed and the testes were excised, trimmed of fat, and weighed. One testis was examined histologically and rated for spermatogenic potential using the Spermatogenic Index (J. M. Whitsett, P. F. Noden, J. Cherry and A. D. Lawton, *J. Reprod. Fertil.*, 72, 277 (1984), which is a semiquantitative estimate of the sperm producing ability of the testes. The index is based on histological appearance of the spermatogenic cells in the seminiferous tubules. A scale of 1 to 6 is used with 5 to 6 being the normal status. A second assessment was based on the weight of the testes.

Figure 1:
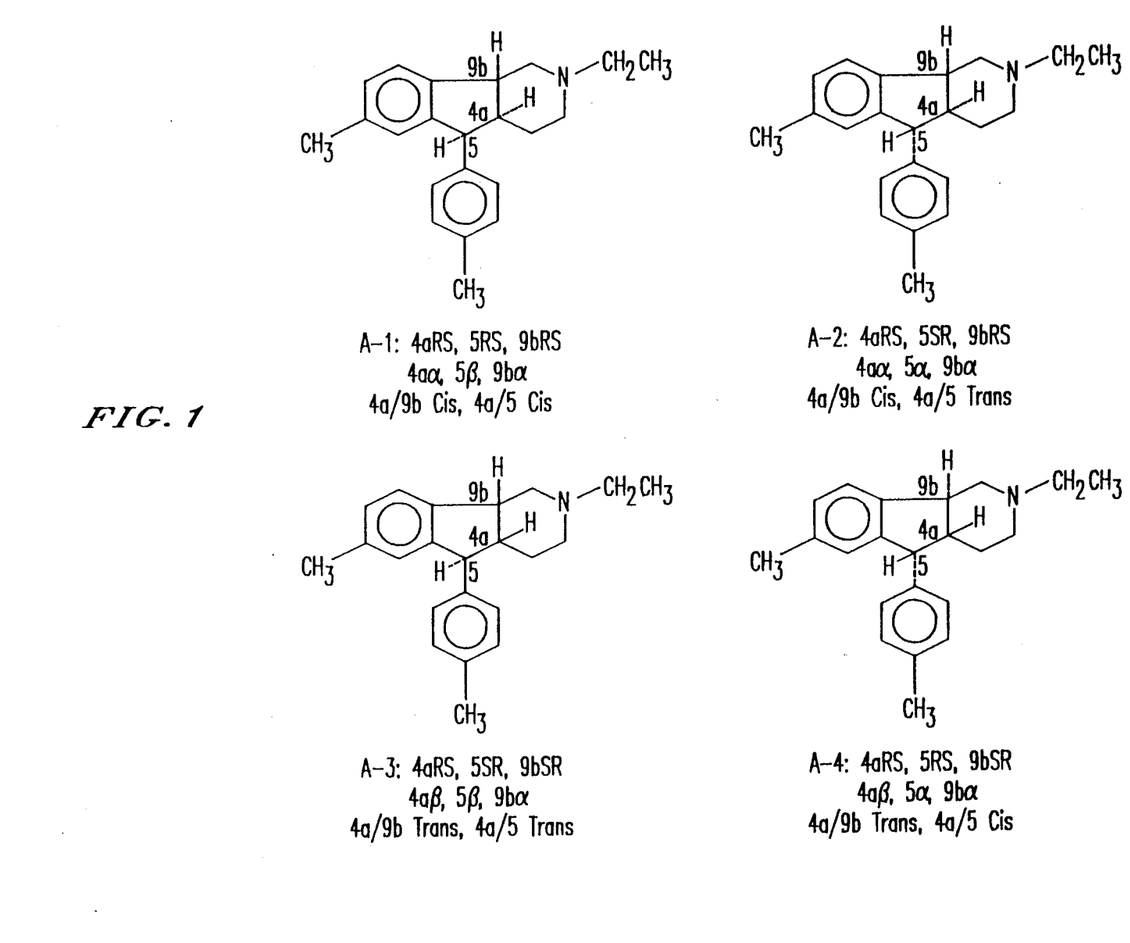
FIGS. 1 and 2 show the structures of some of the compounds of the present invention and comparative compounds.
Figure 2:
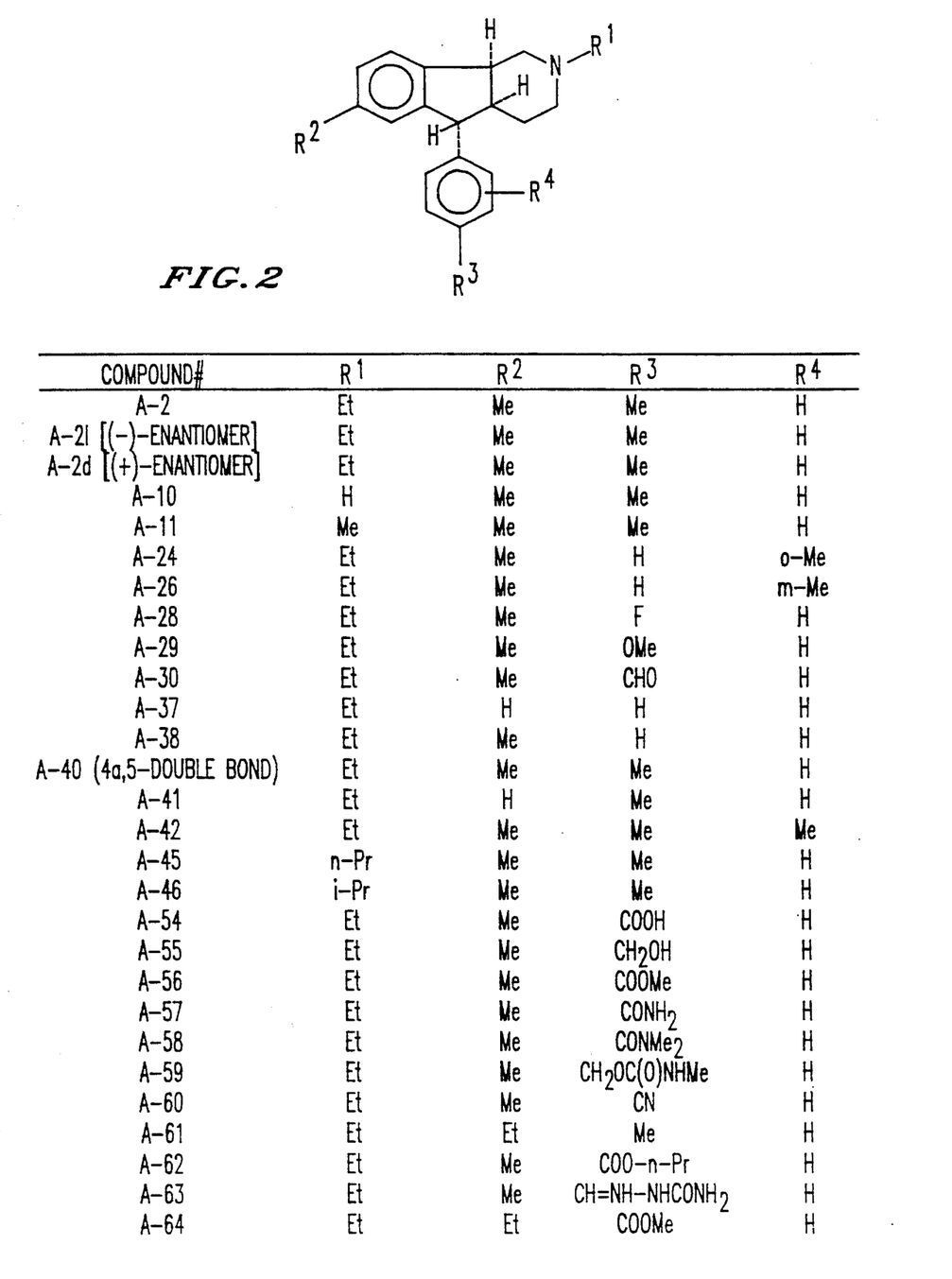

FIGS. 1 and 2 show the structures of specific compounds referred to below and Table 1 shows pertinent biological results. A high degree of stereoselectivity was established by finding that the diastereoisomer of A-2 with all hydrogens cis (A-1) was ineffective at 90 mg/kg as was the diastereoisomeric compound in which the 4a,9b-ring junction is trans and the 4a-H and 5-H are cis (A-3). Further indication of the importance of stereochemistry is the lack of activity, at 90 mg/kg, of the compound in which the 4a,5 position contains a double bond (A-40), thus flattening the molecule from the configuration of A-2. Resolution of A-2 showed pronounced enantioselectivity. The (−)-enantiomer of A-2 (A-21) was found to be completely inactive at 90 mg/kg, whereas the (+)-enantiomer (A-2d) is strongly active at 3 to 10 mg/kg.

The effects of indenopyridine A-56 on fertility immediately after a 35 day course of treatment are shown in Table 2. Oral A-56 was given for 35 days. On the next day male mice were cohabited with females (2 each) for a period of 5 days. Each morning, females were checked for vaginal plugs. The Pregnancy Index is shown in Table 2, column 7. In the mid-dose group for A-56 (7.5 mg/kg/day) two litters were born. Of the two males, siring one litter each, one had a Spermatogenic Index of 4.5, the highest individual score in the group killed at 7 days post drug withdrawal. The high dose group sired no litters and had an average Spermatogenic Index of 1.6. However, this group had as many copulatory plugs as any of the other groups (Table 2, footnote e), thus showing that mating occurred.

The pups sired by males treated with A-2d (2 mg) or A-56 (3.75 or 7 mg/kg/day) were normal, healthy pups. The pups weighed at 7 days appeared to be growing normally (similar to controls).

When mice were treated with A-2 (30 mg/kg PO) serum testosterone concentrations 72 h later of 2.43±1.24 ng/mL did not differ significantly (NS) from concentrations of 3.55±2.65 ng/mL for controls treated with normal saline. If the mice were challenged with 10 IU of human chorionic gonadotropin (hCG) 1 h prior to sacrifice, testosterone concentrations were 52.1±5.7 ng/mL for A-2 treated animals vs. 41.4±5.4 ng/mL for controls (NS). Similar results were obtained when mice were dosed daily for 15 or 30 days with A-2d (Table 3). This is consistent with the lack of effect on libido of A-56 as indicated by copulatory plugs (Table 2, footnote e).

Initial studies with A-2 used oral doses which did not cause any major observable clinical signs in the mice, although they appeared sedated for a short time after dosing. However when subcutaneous doses of A-2 or A-2d were given, very marked, dose-related lethargy was observed. These compounds were less effective as antispermatogenic agents when they were given subcutaneously. At effective oral antispermatogenic doses of 30 mg/kg, none of the compounds of the invention (e.g., A-30, A-54, A-55, A-56 or A-62) were sedative. See Table 4. However when the compounds were given subcutaneously, a sedative effect was seen to a mild extent with all but the aldehyde A-30, the methyl ester A-56, and the carboxylic acid A-54. There were no other obvious signs of toxicity. When mice were treated with A-2d for 30 days at 3 mg/kg/day PO, body weights were not different from those of controls, even though this treatment regimen reduced the Spermatogenic Index from 6.0 in controls to 2.9 in treated animals.

Compound A-56 was given daily to male rats at doses of 10 and 100 mg/kg/day in a toxicology study. This study demonstrated that A-56 was a very effective antispermatogenic agent in rats at doses of 10 and 100 mg/kg/day over a 28-day period. On the basis of the observations of the Spermatogenic Index, it appears that lower doses would still be effective. Except for epididymal hypospermia and the effects on the testis, no specific organ effects were observed in histopathology studes. Clinical chemistry and hematological parameters were unaffected by the treatment. In particular, the compound did not affect epithelial tissue such as intestine, nor did it have any effect on bone marrow. Neurological function, other than enhanced docility, was not significantly affected by the treatment. Any differences were pharmacologic in nature and may be due to the antihistamine-like structure of A-56. During the initial days of dosing, mild to moderate lethargy occurred shortly after dosing. In addition, lower consumption of feed and water occurred during days 1 through 7 and, as a result, body weight gain was reduced. The feed and water consumption and body weight gain rate were all dose related. Tolerance to these effects developed, so that weight gains were equivalent among treatment and control groups during the second, third, and fourth weeks, and overt lethargy was no longer observed after ten days of dosing.

Figure 3:
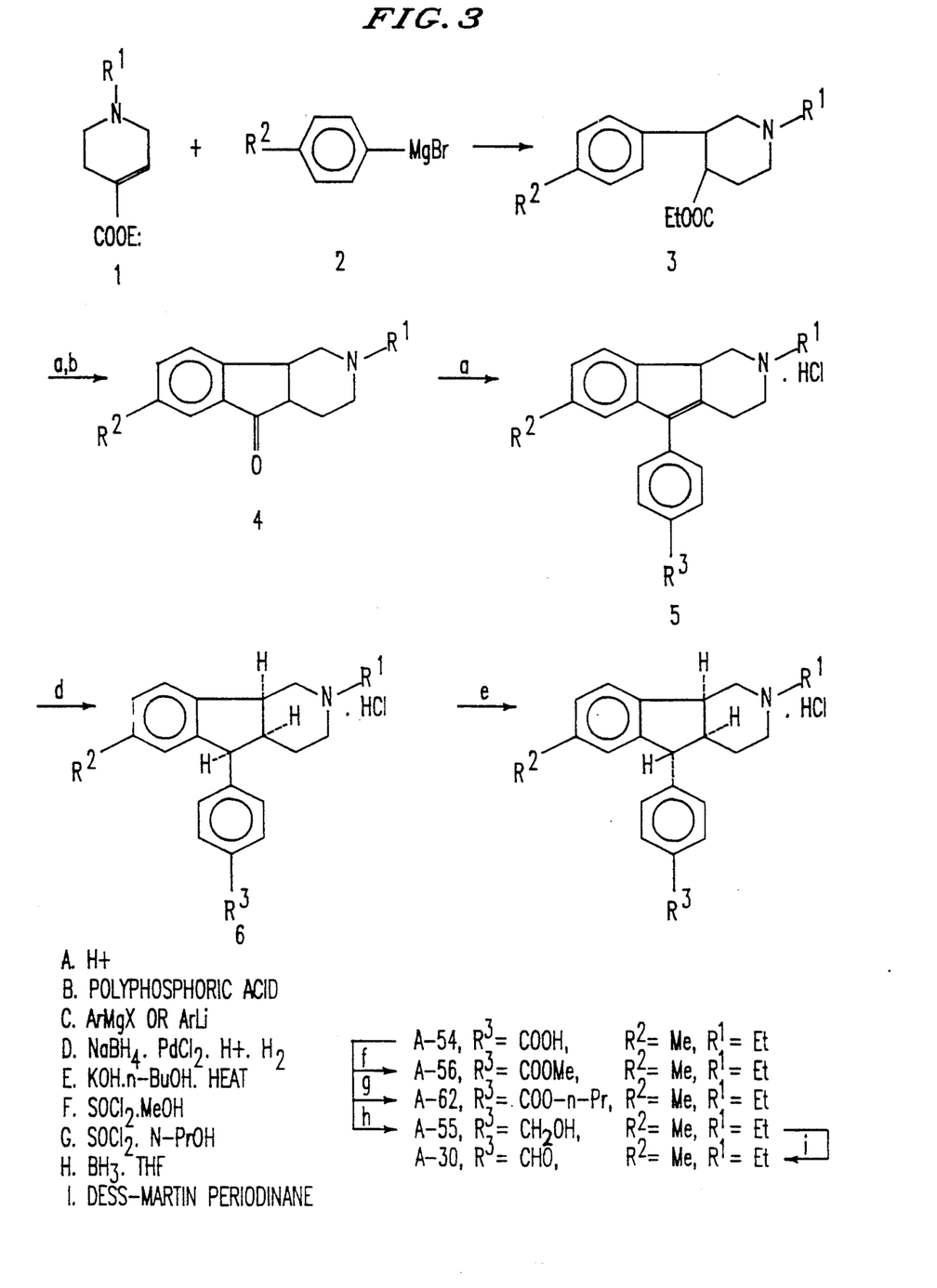
FIG. 3 shows a general synthetic method for preparing the compounds of the present invention.

The compounds of the present invention can be prepared as shown in FIG. 3 using modifications of the method disclosed by Ebenother et al (U.S. Pat. No. 3,678,057). The $R^3$ substituents are introduced into the molecule by using an appropriate Grignard reagent or phenyl lithium reagent in step (c). The mixtures of enantiomers produced by this process are resolved into pure enantiomers by salt formation followed by selective crystallization or chromatography. For example, resolution can be effected by salt formation with S(+) and R(−)-2,2′-(1,1′-binaphthyl)phosphoric acid. Optical purity is established by high pressure liquid chromatography (HPLC) on a CHIRACEL-OD column.

The compounds of the present invention are useful as male antifertility drugs for controlling fertility in mammals, including humans. In addition to their potential use in family planning, the compounds of the invention are also useful to control fertility in domestic, wild or feral animals, where lethal measures are not practical or desirable. For example, the control of deer populations is a problem in some areas of the United States. Oral administration of the compounds of the present invention to seasonal breeding animals such as deer by means of baited feed containing these compounds at appropriate times would substantially reduce reproductive capacity. Other target animals include rodents such as mice, rats, prairie dogs, etc., as well as feral goats, swine, horses, etc. Administration of the compounds of this invention to captive zoo animals provides a means of controlling reproduction in species which become overpopulated.

For the above-mentioned uses, the dose of the compound of the invention will naturally vary depending on the specific compound employed, the mode of administration and the length of infertility desired. However, satisfactory results are obtained in animals at oral doses from about 0.5 to about 50 mg/kg, preferably about 1-30 mg/kg body weight per day. For larger animals, a daily dose amount of about 10-100 mg/kg may be administered as a single oral unit dose or in divided dosage units containing about 1-50 mg of the compound of the present invention. If desired or necessary, the compounds of the invention may be administered together with solid or liquid carriers or diluents or in slow-release form. Formulation of these pharmaceuticals forms is well known in the art and any conventional method of preparing solid, liquid and slow-release formulations may be used with the compounds of the present invention.

Other features of the present invention will become apparent in the course of the following descriptions of exemplary embodiments which are given for illustration of the invention and are not intended to be limiting thereof.

TABLE 1

TESTICULAR RESPONSE TO SELECTED INDENOPYRIDINE ANALOGS IN SWISS (CD-1) MICE[a]

| Test Compound | Dose (mg/kg) | Testes Weight | Spermatogenic Index |
|---|---|---|---|
| Control[b] | 0 | 201.9 ± 11.0 | 5.5 ± 0.16 |
| A-3 | 3 | 190.5 ± 14.8 | 5.2 ± 0.34 |
|  | 10 | 189.2 ± 3.7 | 3.8 ± 0.20* |
|  | 30 | 147.9 ± 15.8* | 2.5 ± 0.32* |
| A-2L | 90# | 223.7 ± 4.60 | 6.0 ± 0.00 |
| A-2D | 1 | 188.2 ± 12.5 | 5.1 ± 0.43 |
|  | 3 | 197.3 ± 14.6 | 3.7 ± 0.12* |
|  | 10 | 134.4 ± 9.4* | 1.7 ± 0.12* |
| A-11 | 3 | 189.1 ± 19.2 | 6.0 ± 0.00 |
|  | 10 | 191.3 ± 24.1 | 4.3 ± 0.46 |
|  | 30 | 167.6 ± 3.8 | 3.6 ± 0.40* |
| A-38 | 3 | 188.7 ± 10.9 | 5.0 ± 0.32 |
|  | 10 | 213.8 ± 15.9 | 5.2 ± 0.12 |
|  | 30 | 189.6 ± 9.3 | 5.4 ± 0.25 |
|  | 90 | 251.2 ± 8.5 | 6.0 ± 0.00 |
| A-41 | 10 | 208.1 ± 17.0 | 6.0 ± 0.00 |
|  | 30 | 213.0 ± 15.6 | 4.8 ± 0.37 |
|  | 90 | 186.3 ± 16.6 | 3.6 ± 0.29* |
| A-42 | 10 | 218.4 ± 11.3 | 6.0 ± 0.00 |
|  | 30 | 206.5 ± 10.6 | 5.8 ± 0.20 |
|  | 90 | 195.1 ± 18.4 | 4.2 ± 0.10* |
| A-46 | 10 | 203.5 ± 14.6 | 5.4 ± 0.38 |
|  | 30 | 187.3 ± 19.0 | 4.3 ± 0.44 |
|  | 90 | 169.5 ± 7.7 | 3.3 ± 0.12* |
| A-54 | 3 | 182.9 ± 8.3 | 5.4 ± 0.29 |
|  | 10 | 159.5 ± 19.0 | 3.5 ± 0.32* |
|  | 30 | 138.2 ± 10.6* | 2.5 ± 0.00* |
| A-55 | 3 | 202.4 ± 8.4 | 5.8 ± 0.2 |
|  | 10 | 182.7 ± 11.5 | 4.4 ± 0.10* |
|  | 30 | 139.3 ± 5.5* | 2.5 ± 0.0* |
| A-56 | 3 | 199.5 ± 12.9 | 5.2 ± 0.25 |
|  | 10 | 174.2 ± 5.9 | 4.0 ± 0.22* |
|  | 30 | 145.0 ± 9.7* | 2.5 ± 0.00* |
| A-62 | 3 | 188.3 ± 11.1 | 5.4 ± 0.24 |
|  | 10 | 205.4 ± 10.1 | 3.7 ± 0.12* |
|  | 30 | 125.5 ± 5.4* | 2.7 ± 0.12* |

[a]Numbers are mean ± standard error of the mean. The number of observations equals 5 unless otherwise stated. A single dose was given orally and the animals killed 72 hr later.
[b]Control data are for vehicle-dosed animals. They are typical and are taken from a dose-response study in which A-2, A-2D, A-54, A-55, A-56, and A-62 were directly compared (data of this table).
*Significantly different from control (Dunnett's one-tailed t-test, p < .05).
N = 4

TABLE 2

TESTICULAR WEIGHTS, SPERMATOGENIC INDEX AND FERTILITY OF MALE CD-1 MICE TREATED WITH CONTRACEPTIVE AGENTS CONTRACEPTIVE EXPERIMENT #2[a]

| Test Compound | Dosage (mg/kg) | Testes Weights (mg) | | | Spermatogenic Index[c] | Pregnancy Index[d] | No[e] Litters |
|---|---|---|---|---|---|---|---|
|  |  | Left[c] | Right[c] | Total[c] |  |  |  |
| Control | 0.0 | 118.16 ± 8.18 | 127.26 ± 8.33 | 245.42 ± 16.30 | 6.00 ± 0.00 | 18/18 (100%) | 18 |
| A-2D | 2.0 | 90.56 ± 4.53 | 95.46 ± 7.39 | 186.02 ± 11.52 | 5.60 ± 0.29 | 16/18 (89%) | 16 |
| A-56[b] | 3.75 | 110.00 ± 7.19 | 109.08 ± 12.36 | 219.08 ± 18.90 | 5.50 ± 0.50 | 16/16 (100%) | 16 |
| A-56 | 7.5 | 56.10 ± 3.51 | 58.60 ± 4.60 | 114.70 ± 7.00 | 3.00 ± 0.52 | 2/20 (10%) | 2 |
| A-56 | 15.0 | 53.36 ± | 55.58 ± | 108.94 ± | 1.60 ± | 0/18 | 0 |

TABLE 2-continued

TESTICULAR WEIGHTS, SPERMATOGENIC INDEX AND FERTILITY OF MALE CD-1 MICE TREATED WITH CONTRACEPTIVE AGENTS CONTRACEPTIVE EXPERIMENT #2[a]

| Test Compound | Dosage (mg/kg) | Testes Weights (mg) | | | Spermatogenic Index[c] | Pregnancy Index[d] | No[e] Litters |
|---|---|---|---|---|---|---|---|
| | | Left[c] | Right[c] | Total[c] | | | |
| | | 6.42 | 4.65 | 11.01 | 0.10 | (0%) | |

[a]FIGS. are means ± standard error of the mean (n = 5). Animals (8 to 10 per group) were treated daily (orally by gavage) for 35 days and one half in each group were sacrificed seven days after the last day of treatment.
[b]n = 4.
[c]ANOVA (p < 0.05) detected a significant difference between test compounds. For testes weights, A-2D, 056 (7.5 mg/kg), and 056 (15.0 mg/kg) were significantly lower than controls (Dunnett's one-tailed t-test, p < 0.05). For Spermatogenic Index, and testes weights 056 (7.5 mg/kg) and 056 (15.0 mg/kg) were significantly lower than controls.
[d]Each male was housed with 2 females beginning one day after the last dose. This index is based on a potential of 100%. The denominator is the number of females; the numerator is the number of litters born.
[e]Number of litters per treatment group. In spite of the lack of conception in the mid and high dose groups, evidence of mating was present (vaginal copulatory plugs) in 13/18, 11/18, 11/16, 14/20, and 14/18 for the 5 groups of animals.

TABLE 3

The Endocrine Response of the Testes to Gonadotropin Stimulus (hCG) after Treatment with 1, 15, or 30 Daily Doses of A-2D in Swiss Mice

| Treatment/dose | Saline | hCG |
|---|---|---|
| 15 day treatment: | | |
| Vehicle control | 0.83 ± 0.34[d] | 63.69 ± 13.14 |
| A-2D (10 mg/kg)[c] | 5.43 ± 2.28 | 75.15 ± 10.76 |
| A-2D (0.5 mg/kg) | 0.38 ± 0.04 | 59.61 ± 6.59 |
| A-2D (1.0 mg/kg) | 3.51 ± 3.11 | 65.59 ± 4.98 |
| A-2D (3.0 mg/kg) | 0.34 ± 0.05[d] | 54.14 ± 6.51[d] |
| 30 day treatment: | | |
| Vehicle control | 0.46 ± 0.09 | 45.86 ± 8.11 |
| A-2D (10 mg/kg)[c] | 1.10 ± 0.71 | 45.44 ± 9.77 |
| A-2D (0.5 mg/kg) | 1.30 ± 1.07 | 36.65 ± 4.64 |
| A-2D (1.0 mg/kg) | 4.14 ± 3.90 | 41.92 ± 4.03 |
| A-2D (3.0 mg/kg) | 0.22 ± 0.04[d] | 42.26 ± 7.48[d] |

[a]FIGS. are means ± standard error of the mean. n = 5 unless otherwise noted. Animals were treated daily PO for either 15 or 30 days.
[b]Statistical analyses were ANOVA (p < 0.05) with duration of treatment, treatment, challenge, duration × treatment, duration × challenge, treatment × challenge and duration × treatment × challange interaction used as sources of variation. Data were converted to logarithms (log10) prior to analysis. ANOVA detected a significant response of testosterone to duration of treatment, treatment, and challenge.
However, the "treatment" effect was due to differences in the saline treated group (i.e., normal baseline variation among animals). Analysis of the hCG group alone did not detect an effect of treatment (dose) while duration was still significant (SAS, 1990).
[c]Positive control, animals received one dose only on Day 1.
[d]n = 4.

TABLE 4

CLINICAL SIGNS IN SWISS MICE TREATED WITH INDENOPYRIDINES[a]

| Test Compound | Dosage (mg/kg) | Route of Administration[a] | |
|---|---|---|---|
| | | PO[b] | SC Injection[c] |
| Vehicle Control | 0 | = | = |
| 2 | 30 | + | +++ |
| 2D | 10 | ++ | +++ |
| 2L | 10 | = | = |
| 55 | 30 | = | ++ |
| 30 | 30 | = | = |
| 54 | 30 | = | ?[d] |
| 56 | 30 | = | = |
| 62 | 30 | = | ++ |

[a]This is a summary of data from several trials. Animals dosed once and sacrificed 72 h post-treatment. Abbreviations are
= (No post-treatment lethargy),
+ (15–60 min post-treatment lethargy),
++ (60 min to 3 h post-treatment lethargy), and
+++ (3–6 h post-treatment lethargy, reduced body temperature). Animals appeared normal 24 h post-treatment.
[b]PO = by gavage per os at 10 ml/kg body weight
[c]SC = subcutaneous
[d]Conflicting observations were recorded in two separate studies (= in one, + in one).

EXAMPLES

EXAMPLE 1. Synthesis of 2-Ethyl-7-methyl-2,3,4,4a,α,5,9bα-hexahydro-5α-(p-carboxyphenyl)-1H-indeno[1,2-c]pyridine Hydrochloride (A-54).

Iodoethane (540 g, 3.41 mol) in methanol (500 mL) was added to ethyl isonicotinate (500 g, 3.31 mol). The mixture was refluxed gently overnight. Sodium borohydride (140 g) was added portionwise to the above solution under cooling (ice bath). After the addition of $NaBH_4$ was complete, the mixture was stirred at room temperature overnight. Most of the methanol was evaporated, water and ether were added to the solution and ether layer was separated. Evaporation of dry ether ($Na_2SO_4$) layer gave an oil. Distillation of this red oil gave a yellowish oil (Compound 1 of FIG. 3, $R^1$=Et, 470 g, 78%): bp 160° C. at 0.5 mm.

The above compound (146 g, 0.8 mol) in dry ether (200 mL) was added dropwise to 1M p-tolylmagnesium bromide (Compound 2 of FIG. 3, $R^2$=Me) in ether (600 mL, 1.6 mol). After being stirred for 3 h, the reaction mixture was poured into 10% aqueous $NH_4Cl$ solution (200 mL). The aqueous layer was extracted with ether. Evaporation of the dry ($Na_2SO_4$) ether layer gave a yellowish brown oil (Compound 3 of FIG. 3, $R^1$=Et, $R^2$=Me). This oil was dissolved in 18% aqueous HCl (500 mL) and extracted with ether. The aqueous HCl solution of crude 3 was refluxed for 2 h. Evaporation of the solvent gave the corresponding amino acid (181 g, yield 80%), which (32 g) was mixed with polyphosphoric acid (500 g) and stirred vigorously at 140° C. for 3 h. The reaction mixture was cooled and 50% KOH aqueous solution was added cautiously. The basified solution was extracted with ether. Evaporation of the dry ($Na_2SO_4$) ether layer gave 2-ethyl-7-methyl-2,3,4,4aα,5,9bα-hexahydro-1H-indeno[1,2-c]pyridin-5-one (Compound 4 of FIG. 3, $R^1$=Et, $R^2$=Me) as an oil (22.6 g, 87%). An analytical sample of 4 was obtained by passing through a small column of $SiO_2$ using a gradient of MeOH in $CHCl_3$ (0-5%): $^1H$ NMR (90 MHz, $CDCl_3$) δ 7.5 (1H, s, H-6), 7.3 (2H, m, H-8, H-9), 3.5 (1H, m), 3.0 (1H, m), 2.6 (2H, m), 2.3 (3H, s, 7-Me), 2.2 (3H, m), 1.9–1.7 (3H, m), 1.1 (3H, t, Me); HRMS (M+): Calcd. for $C_{15}H_{19}NO$: m/z 229.1467. Found: m/z 229.1466.

To a mechanically stirred solution of parabromobenzoic acid (1.6 g, 8.0 mmol) in tetrahydrofuran (THF) (15 mL) at −78° C. was added n-butyllithium (16.2 mmol, 6 mL of a 2.5M solution in hexane) dropwise over a 45 min period. After the mixture was stirred for an additional 1.5 h, tricyclic ketone 4 (1.1 g, 5.1 mmol) was added as a solution in THF (5 mL) dropwise over a 30 min period and stirring was continued for 2.5 h at −78° C. The mixture was poured into ice cold 1M HCl (75 mL) and extracted with ether (2×30 mL). The acidic aqueous layer was stirred for 15 h at room temperature and concentrated under reduced pressure to afford a solid. This solid was purified via flash column chromatography on silica with a gradient elution of 10–20% MeOH in $CHCl_3$ and yielded 2-ethyl-7-methyl-2,3,4,9b-tetrahydro-5-(p-carboxyphenyl)-1H-indeno[1,2-c]pyridine hydrochloride (Compound 5, $R^3$=COOH, $R^2$=Me, $R^1$=Et) as a yellow solid (1.1 g, 58%; 85% based on recovered Compound 4). $^1$H NMR (250 MHz, $CDCl_3$), δ 1.54 (3H, t, J=7.2 Hz), 2.35 (3H, bs), 2.25–2.42 (1H, m), 2.50–2.72 (1H, m), 2.94–3.0 (1H, m), 3.15–3.30 (2H, m), 3.50–3.80 (2H, m), 4.17–4.30 (1H, m), 4.40–4.52 (1H, m), 7.0–7.12 (2H, m), 7.32 (1H, d, J=7.5 Hz), 7.45 (2H, d, J=8.4 Hz), 8.20 (2H, d, J=8.4 Hz). HRMS (M+) Calcd. MW for $C_{22}H_{23}NO_2$: m/z 333.1729. Found: m/z 333.1725.

To a solution of the above compound (379 mg, 1.03 mmol) in ethanol/water (40 mL of a 1:1 mixture) was added NaCl (81 mg), $PdCl_2$ (98 mg), $NaBH_4$ (100 mg), and concentrated HCl (10 drops). After the mixture was shaken on a Parr apparatus under a hydrogen atmosphere (45 psi) at 50° C. for 15 h, it was filtered through Celite and concentrated under reduced pressure. The resulting solid was suspended in absolute ethanol, filtered through Celite, and the filtrate was concentrated under reduced pressure to yield 2-ethyl-7-methyl-2,3,4,4aα,5,9bα-hexahydro-5β-(p-carboxyphenyl)-1H-indeno[1,2-c]pyridine hydrochloride (Compound 6 of FIG. 3, $R^3$=COOH, $R^2$=Me, R=Et). $^1$H NMR (250 MHz, $CDCl_3$): δ 1.4 (3H, t, 7.2 Hz), 1.50–1.60 (1H, m), 1.85–2.00 (1H, m), 2.20 (3H, s), 2.20–2.40 (1H, m), 2.70–2.90 (3H, m) 2.90–3.15 (2H, m), 3.50–3.65 (1H, m), 3.90–4.10 (1H, m), 4.50 (1H, d, J=7.3 Hz), 6.95, (1H, bs), 7.10 (1H, d, J=7.5 Hz), 7.20 (1H, d, J=7.5 Hz), 7.30, (2H, d, J=8.0 Hz), 8.00 (2H, d, J=8.0 Hz). HRMS (M+) Calcd. MW for $C_{22}H_{25}NO_2$: m/z 335.18853. Found: m/z 335.1887.

To a solution of potassium hydroxide (15 g) in n-butanol (60 mL) was added the above compound 6 (2.99 g, 8.0 mmol) in one portion. After being refluxed for 20 h, the dark brown mixture was cooled to 0.C and acidified to pH≃1 with 18% HCl. The solvent was removed in vacuo to afford a yellow solid. This solid was taken up in $CHCl_3$, filtered through Celite, and the filtrate was concentrated in vacuo to afford crude 2-ethyl-7-methyl-2,3,4,4aα,5,9bα-hexahydro-5α-(p-carboxyphenyl)-1H-indeno[2,2-c]pyridine hydrochloride as an off-white solid. This solid was purified via flash column chromatography using 10% MeOH—$CHCl_3$ and yielded 1.23 g (41%) of A-54 (FIG. 3) as a white solid. m.p.=280° C. (dec.) $^1$H NMR (250 MHz, $CDCl_3$—$CD_3OD$). δ 1.45 (3H, t, J=7.3 Hz), 1.8 (1H, bd, J=14.7 Hz), 2.2 (3H, s), 2.4–2.7 (2H, m), 3.0–3.4 (4H, m), 3.4–3.7 (2H, m), 3.7–4.0 (1H, m), 4.2 (1H, d, 11 Hz), 6.6 (1H, bs), 7.0–7.2 (4H, m), 8.0 (1H, d, J=7.7 Hz). HRMS (M+) Calcd. MW for $C_{22}H_{25}NO_2$: m/z 335.18853. Found: m/z 335.18830.

Anal. Calcd. for $C_{22}H_{26}ClNO_2 \cdot \frac{1}{2}H_2O$: C, 69.37; H, 7.14; N, 3.68. Found: C, 69.72; H, 7.15; N, 3.55.

EXAMPLE 2.

2-Ethyl-7-methyl-2,3,4,4aα,5,9bα-hexahydro-5α-(p-carbomethoxyphenyl)-1H-indenol[1,2-c]pyridine Hydrochloride (A-56).

To a solution of the carboxylic acid A-54 (3.6 g, 9.69 mmol) in methanol (50 mL) at −10° C. was added thionyl chloride (1.1 mL, 14.5 mmol) over a 10 min period. The resulting solution was allowed to stand in a refrigerator at 5° C. for 68 h during which time the product had begun to crystallize out as fine white needles. Three crops were obtained and combined to yield 2.65 g of A-56 (FIG. 3). mp=204° C. (sublimed). $^1$H NMR (250 MHz, $CDCl_3$): δ 1.1 (3H, t, J=7.2 Hz), 1.6 (1H, bd, J=14.2 Hz), 1.80–2.00 (2H, m), 2.1–2.2 (1H, m), 2.2 (3H, s), 2.4 (2H, q, J=7.2 Hz), 2.5–2.6 (1H, m), 2.7–2.8 (1H, m), 2.9 (1H, dd, J=5.94, 11.64 Hz), 3.3–3.4 (1H, m), 3.9 (3H, s), 4.2 (1H, d, J=10.0 Hz), 6.7 (1H, bs), 7.0 (1H, d, J=7.5 Hz), 7.2 (1H, d, J=7.5 Hz), 7.3 (2H, d, J=8.0 Hz), 8.0 (2H, d, 8.0 Hz).

Anal. Calcd. for $C_{23}H_{28}ClNO_2 \cdot \frac{1}{4}H_2O$: C, 70.75; H, 7.36; N, 3.59. Found: C, 70.67; H, 7.36; N, 3.59.

EXAMPLE 3.

2-Ethyl-7-methyl-2,3,4,4aα,5,9bα-hexahydro-5α-[p-(n-propyloxycarbonyl)phenyl]-1H-indeno[1,2c]pyridine Hydrochloride (A-62).

The carboxylic acid A-54 (83.1 mg, 0.22 mmol) was transformed into the corresponding acid chloride by treatment with thionyl chloride (3 mL) for 3 h at room temperature. Excess thionyl chloride was removed in vacuo and to the remaining material was added n-propanol (3 mL), and the solution was stirred for 4 days at room temperature. The solvent was removed in vacuo, and the crude material was passed through a column of silica gel with chloroform-methanol (20:1) as eluent. Exposure to ethereal hydrogen chloride yielded 90.5 mg (99%) of A-62 (FIG. 3) as a white solid. mp=202° C. (sublimed). $^1$H NMR (250 MHz, $CDCl_3$): δ 1.1–1.4 (6H, m), 1.5–1.7 (3H, m), 1.7–2.0 (2H, m), 2.1–2.2 (1H, m) 2.2 (3H, s), 2.3–2.5 (3H, m), 2.7–2.8 (1H, m), 2.9–3.0 (1H, m), 3.2–3.4 (1H, m), 3.8 (2H, 5, J=7.4 Hz), 4.2 (1H, d, J=10.0), 6.7 (1H, s), 6.9 (1H, d, J=7.5 Hz), 7.1 (1H, d, J=7.5 Hz), 7.2 (2H, d, J=8.0 Hz), 8.0 (2H, d, J=8.0 Hz).

Anal. Calcd. for $C_{22}H_{32}ClNO_2 \cdot \frac{3}{4}H_2O$: C, 70.24; H, 7.90; N, 3.28. Found: C, 70.06; H, 7.76; N, 3.18.

EXAMPLE 4.

2-Ethyl-7-methyl-2,3,4,4aα,5,9bα-hexahydro-5α-(p-hydroxymethylphenyl)-1H-indeno[1,2-c]pyridine Hydrochloride (A-55).

To a slurry of A-54 (175 mg, 0.47 mmol) in tetrahydrofuran THF (1 mL) at 0° C. was added $BH_3$-THF (1 mmol; 1 mL of a 1.0M solution in THF) dropwise over a 10 min period. The resulting mixture was warmed to room temperature and stirred for 5 h at which time it was quenched by the slow addition of 3M NaOH (15 mL) and allowed to stir for 16 h. The solution was saturated with potassium carbonate, extracted with ether (3×30 mL), dried ($Na_2SO_4$), and concentrated in vacuo to afford a white solid which was purified via flash column chromatography using 10% MeOH—$CHCl_2$. The yield of A-55 (FIG. 3) was 117.2 mg (70%). m.p. 218° C. (dec); $^1$H NMR (250 MHz, $CDCl_3$). δ 1.4 (3H, t, J=7.3 Hz), 1.7 (1H, bd, J=14 Hz), 2.2 (3H, s), 2.25–2.4 (1H, m), 2.5–2.9 (4H, m), 2.9–3.5 (5H, m), 4.0–4.2 (1H, m), 4.7 (2H, bs), 6.7 (1H, bs), 7.0–7.4 (6H, m).

Anal. Calcd. for $C_{22}H_{28}ClNO \cdot \frac{1}{4} H_2O$: C, 71.14; H, 8.00; N, 3.77. Found: C, 71.36; H, 7.73; N, 3.74.

EXAMPLE 5.
2-Ethyl-7-methyl-2,3,4,4a$\alpha$,5,9b$\alpha$-hexahydro-5$\alpha$-(p-formylphenyl)-2H-indeno[1,2-c]pyridine Hydrochloride (A-30).

To a solution of A-55 (62.6 mg, 0.18 mmol) in $CH_2Cl_2$ (4 mL) was added Dess-Martin periodinane (300 mg) portionwise until thin layer chromatography (10:1 $CHCl_3$:MeOH on silica gel) indicated that the starting material had been completely consumed (20 min). The reaction mixture was passed through a short column of silica gel with $CH_2Cl_2$ as eluent and the solvent was removed in vacuo to yield 31.6 mg (51%) of A-30 (FIG. 3) as a white solid. m.p. 190° C. (dec); $^1$H NMR (250 MHz, $CDCl_3$). $\delta$ 1.4 (3H, t, J=7.3 Hz), 1.5–1.7 (1H, m), 2.3 (3H, s), 2.6–2.8 (3H, m), 3.0 (2H, q, J=7.3 Hz), 3.1–3.5 (4H, m), 4.1–4.3 (1H, m), 6.7 (1H, bs), 7.0–7.4 (4H, m), 7.8–7.9 (2H, m), 10.0 (1H, s).

Anal. Calcd. for $C_{22}H_{26}ClNO \cdot \frac{1}{4} H_2O$: C, 72.41; H, 7.46; N, 3.84. Found: C, 72.03; H, 7.79; N, 3.80.

EXAMPLE 6. Resolution of Compound A-2.

A-2 as the hydrochloride salt (5.1 g, 15 mmol) was partitioned between ethyl acetate and aqueous ammonia and the organic phase dried over sodium sulfate and evaporated to give 4.5 g of A-2 free base. This material was dissolved in methanol (150 mL) and treated with an equivalent to S-(+)-2,2-(1′,1′-binaphthyl)phosphoric acid (BNPPA) (5.1 g, 14.7 mmol). The mixture was warmed in a water bath to a clear solution. After standing at 4° C. for two days, the white crystals were filtered.

The collected crystals were recrystallized from hot methanol to give 3.55 g of a diastereomeric salt. From this salt, the free base of A-21 was extracted into the organic phase on partitioning between ethyl acetate and aqueous ammonia. The residue from the ethyl acetate extract was acidified with methanolic HCl. The hydrochloride thus obtained (1.75 g) was recrystallized from methanol/ethyl acetate to give 630 mg of colorless crystals. The optical purity was established by chiral high performance liquid chromatography (HPLC) analysis on a chiralcel-OD column (J. T. Baker, Inc.) with an eluting solvent of n-propanol at a flow rate of 0.1 mL per minute. Optical rotation: $[\alpha]_{589} = -1.6°$ (c=0.5, chloroform).

The original mother liquor from the above described separation of A-21 was concentrated and partitioned between ethyl acetate and aqueous ammonia. The residue from the dry organic phase (2.4 g) was dissolved in methanol and treated with an equivalent of R-(−)-BNPPA (2.75 g, 7.9 mmol. After two days at 4° C., crystals were collected and washed with cold methanol. The collected crystals were recrystallized from hot methanol to give the diastereomeric salt (3.85 g). The salt was partitioned between ethyl acetate and aqueous ammonia and the ethyl acetate extract was dried and concentrated to give A-2d free base (1.8 g), which was converted to the hydrochloride and recrystallized from methanol/ethyl acetate as described above to give 650 mg of A-2d hydrochloride as colorless crystals. The optical purity of A-2d was confirmed by chiral HPLC analysis as described above for A-21. Optical rotation: $[\alpha]_{589} = 1.6°$ (c=0.5, chloroform).

Obviously, numerous modifications and variations of the present invention are possible in light of the above teachings. It is therefore to be understood that, within the scope of the appended claims, the invention may be practiced otherwise than as specifically described herein.

I claim:

1. A compound having the formula wherein said compound has the relative stereochemistry shown in formula (I) or is the enantiomer thereof, wherein $R^1$ is a straight-chain or branched $C_{1-6}$ alkyl, $R^2$ is hydrogen, straight-chain or branched $C_{1-6}$ alkyl and $R^3$ is CHO, $CH_2OH$, COOR where R is $C_{1-10}$ alkyl, $C_{6-10}$ aryl or $C_{7-10}$ aralkyl, or $R^3$ is $CH_2OC(O)R$ where R is as defined above which is metabolized or converted to a carboxyl group under mammalian physiological conditions, mixtures of said compound and enantiomers thereof, and acid addition salts thereof.

2. The compound of claim 1, wherein $R^3$ is COOR where R is $C_{1-3}$ alkyl.

3. The compound of claim 2, wherein R is methyl.

4. The compound of claim 1, wherein $R^3$ is hydroxymethyl.

5. The compound of claim 1, wherein $R^3$ is formyl.

6. The compound of claim 1, wherein $R^3$ is $CH_2OC(O)R$ where R is $C_{1-6}$ alkyl.

7. The compound of claim 1, wherein $R^1$ is $C_{1-3}$ alkyl.

8. The compound of claim 1, wherein $R^2$ is $C_{1-3}$ alkyl.

9. The compound of claim 1, wherein $R^2$ is hydrogen.

10. The compound of claim 1, wherein said compound is a single enantiomer and possesses antispermatogenic activity.

11. The compound of claim 1, wherein said compound is a mixture of two enantiomers.

12. A pharmaceutical composition comprising an antispermatogenically effective amount of the compound of claim 1 and a carrier or diluent.

13. The composition of claim 12, wherein in said compound, $R^3$ is CHO, $CH_2OH$, COOR where R is $C_{1-10}$ alkyl, $C_{6-10}$ aryl or $C_{7-10}$ aralkyl or $R^3$ is $CH_2OC(O)R$ where R is as defined above.

14. The composition of claim 12, wherein $R^3$ is hydroxymethyl.

15. The composition of claim 12, wherein $R^3$ is formyl.

16. The composition of claim 12, wherein $R^3$ is methoxycarbonyl.

17. The composition of claim 12, wherein said compound is a single enantiomer and possesses antispermatogenic activity.

18. The composition of claim 12, wherein said compound is a mixture of two enantiomers.

19. A method of inhibiting spermatogenesis in a mammal, comprising administering to said mammal an antispermatogenically effective amount of the compound of claim 1.

20. The method of claim 19, wherein $R^3$ is CHO, $CH_2OH$, COOR where R is $C_{1-10}$ alkyl, $C_{6-10}$ aryl or $C_{7-10}$ aralkyl or $CH_2OC(O)R$ where R is as defined above.

21. The method of claim 19, wherein $R^3$ is hydroxymethyl.

22. The method of claim 19, wherein $R^3$ is formyl.

23. The method of claim 19, wherein $R^3$ is metoxycarbonyl.

24. The method of claim 19, wherein said mammal is a human.

25. The method of claim 19, comprising oral administration at a dose of 0.5–50 mg/kg/da.

26. The method of claim 19, wherein said compound is a single enantiomer and possesses antispermatogenic activity.

27. The method of claim 19, wherein said compound is a mixture of two enantiomers.

28. A substantially pure compound having the formula wherein said compound has the relative stereochemistry shown in formula (I) or is the enantiomer thereof, wherein $R^1$ is straight-chain or branched $C_{1-6}$ alkyl, $R^2$ is hydrogen, straight-chain or branched $C_{1-6}$ alkyl and $R^3$ is carboxyl, mixtures of said compound and the enantiomer thereof, and salts thereof.

29. A pharmaceutical composition comprising an antispermatogenically effective amount of the compound of claim 28 and a carrier or diluent.

30. A method of inhibiting spermatogenesis in a mammal, comprising administering to said mammal an antispermatogenically effective amount of the composition of claim 29.

31. The method of claim 30, wherein said mammal is a human and said compound is orally administered at a dose of 0.5–50 mg/kg/da.

* * * * *

UNITED STATES PATENT AND TRADEMARK OFFICE
CERTIFICATE OF CORRECTION

PATENT NO. : 5,319,084

DATED : June 7, 1994

INVENTOR(S) : C. Edgar COOK, et al

It is certified that error appears in the above-identified patent and that said Letters Patent is hereby corrected as shown below: Delete FIG. 2 in its entirety and replace with FIG. 2:

FIGURE 2
STRUCTURES OF SOME TESTED COMPOUNDS
(relative stereochemistry only is shown)

| Compound # | $R^1$ | $R^2$ | $R^3$ | $R^4$ |
|---|---|---|---|---|
| A-2 | Et | Me | Me | H |
| A-2l [(-)-enantiomer] | Et | Me | Me | H |
| A-2d [(+)-enantiomer] | Et | Me | Me | H |
| A-10 | H | Me | Me | H |
| A-11 | Me | Me | Me | H |
| A-24 | Et | Me | H | o-Me |
| A-26 | Et | Me | H | m-Me |
| A-28 | Et | Me | F | H |
| A-29 | Et | Me | OMe | H |
| A-30 | Et | Me | CHO | H |
| A-37 | Et | H | H | H |
| A-38 | Et | Me | H | H |
| A-40 (4a,5-double bond) | Et | Me | Me | H |
| A-41 | Et | H | Me | H |
| A-42 | Et | Me | Me | o-Me |
| A-45 | n-Pr | Me | Me | H |
| A-46 | i-Pr | Me | Me | H |
| A-54 | Et | Me | COOH | H |
| A-55 | Et | Me | $CH_2OH$ | H |
| A-56 | Et | Me | COOMe | H |
| A-57 | Et | Me | $CONH_2$ | H |
| A-58 | Et | Me | $CONMe_2$ | H |
| A-59 | Et | Me | $CH_2OC(O)NHMe$ | H |
| A-60 | Et | Me | CN | H |
| A-61 | Et | Et | Me | H |
| A-62 | Et | Me | COO-n-Pr | H |
| A-63 | Et | Me | $CH=NH-NHCONH_2$ | H |
| A-64 | Et | Et | COOMe | H |

UNITED STATES PATENT AND TRADEMARK OFFICE
CERTIFICATE OF CORRECTION

PATENT NO. : 5,319,084

DATED : June 7, 1994

INVENTOR(S) : C. Edgar COOK, et al

It is certified that error appears in the above-identified patent and that said Letters Patent is hereby corrected as shown below: Delete FIG. 3 in its entirety and replace with FIG. 3:

FIGURE 3 a. H+
b. polyphosphoric acid
c. ArMgX or ArLi
d. NaBH4, PdCl2, H+, H2
e. KOH, n-BuOH, heat
f. SOCl2, MeOH
g. SOCl2, n-PrOH
h. BH3 • THF
i. Dess-Martin periodinane A-54. R3 = COOH, R2 = Me, R1 = Et
A-56. R3 = COOMe, R2 = Me, R1 = Et
A-62. R3 = COO-n-Pr, R2 = Me, R1 = Et
A-55. R3 = CH2OH, R2 = Me, R1 = Et
A-30. R3 = CHO, R2 = Me, R1 = Et

UNITED STATES PATENT AND TRADEMARK OFFICE
CERTIFICATE OF CORRECTION

PATENT NO. : 5,319,084

DATED : June 7, 1994

INVENTOR(S) : C. Edgar COOK, et al.

It is certified that error appears in the above-identified patent and that said Letters Patent is hereby corrected as shown below:

Column 2, line 16, "e regulation" should read --(e) regulation--.

line 47 "no. 20,438" should read --no. 20-438--.

Column 4, line 56, "pysiological" should read --physiological--.

Column 5, line 53, "A-2 (A-21)" should read --A-2(A-2$\ell$)--.

Column 6, line 49, "studes" should read --studies--.

Column 10, line 21, "2-Ethyl-7-methyl-2,3,4,4a,$\alpha$, 5,9b$\alpha$-hexahydro-5$\alpha$-(p-"

should read --2-Ethyl-7-methyl-2,3,4, 4a$\alpha$,5,9b$\alpha$-hexahydro-5$\alpha$-[p- --.

Column 11, line 6, "for 15 h at room tem-"

should read --for 15h at reflux tem- --.

line 7 "perature and" should read --perature (ca.100°C) and--.

line 49, "0.C" should read --0°C--.

line 55, "phenyl)-1H-indeno[2,2-c]pyridine hydrochloride as an"

should read --phenyl)-1H-indeno[1,2-c]pyridine hydrochloride as an--.

UNITED STATES PATENT AND TRADEMARK OFFICE
CERTIFICATE OF CORRECTION

PATENT NO. : 5,319,084
DATED : June 7, 1994
INVENTOR(S) : C. Edgar COOK, et al.

It is certified that error appears in the above-identified patent and that said Letters Patent is hereby corrected as shown below:

Column 12, line 26, "propyloxycarbonyl)phenyl]-1H-indeno[1,2c]pyridine"

should read --propyloxycarbonyl)phenyl]-1H-indeno[1,2-c]pyridine--.

line 65, "H-CHCl$_2$" should read --H-CHCl$_3$--.

Column 15, line 11, "R$^3$ is metoxycar-" should read --R$^3$ is methoxycar- --.

Signed and Sealed this

Fourteenth Day of July, 1998

Attest:

BRUCE LEHMAN

*Attesting Officer*      *Commissioner of Patents and Trademarks*